United States Patent [19]

Pickart

[11] Patent Number: 4,877,770
[45] Date of Patent: Oct. 31, 1989

[54] CHEMICAL DERIVATIVES OF GHL-CU

[75] Inventor: Loren R. Pickart, Bellevue, Wash.

[73] Assignee: ProCyte Corporation, Redmond, Wash.

[21] Appl. No.: 312,295

[22] Filed: Feb. 17, 1989

Related U.S. Application Data

[63] Continuation of Ser. No. 40,460, Apr. 20, 1987, abandoned, which is a continuation-in-part of Ser. No. 699,824, Feb. 8, 1985, Pat. No. 4,665,054.

[51] Int. Cl.$^4$ .......................... A61K 37/02; C07K 5/08
[52] U.S. Cl. ........................................ 514/18; 530/331
[58] Field of Search ........................... 514/18; 530/331

[56] References Cited

U.S. PATENT DOCUMENTS

| | | | |
|---|---|---|---|
| 3,194,732 | 7/1965 | Neuhauser | 167/58 |
| 3,551,554 | 12/1970 | Herschler | 424/7 |
| 3,558,770 | 1/1971 | Gordon et al. | 424/80 |
| 3,758,682 | 9/1973 | Huber et al. | 424/28 |
| 3,832,338 | 8/1974 | Huber et al. | 530/401 |
| 4,022,888 | 5/1977 | Huber et al. | 514/21 |
| 4,167,945 | 9/1979 | Gottlieb | 121/334 R |
| 4,263,428 | 4/1981 | Apple et al. | 536/17 |
| 4,287,184 | 9/1981 | Young | 514/21 |
| 4,440,788 | 4/1984 | Terayama et al. | 424/320 |
| 4,665,054 | 5/1987 | Pickart | 514/18 |

OTHER PUBLICATIONS

Pickart et al., "Growth-Modulating Tripeptide (glycylhistidylysine): Association with Copper and Iron in Plasma and Stimulation of Adhesive and Growth of Hepatoma Cells in Culture by Tripeptide-Metal Ion Complexes," *J. Cell, Physiol.*, 102(2), pp. 129–139, 1980, (Cited in Chem. Abstracts, vol. 93: 1155m, 1980).
Williams et al., "Glycyl-L-Histidyl-L-Lysine, a Growth Promoting Factor for Human Cells," Cytobios., 27(105), pp. 19–25, 1980, (Cited in Chem. Abstracts, vol. 94:25451b, 1981).
Mochida Pharmaceutical Co., Ltd., "Antiinflammatory Injections Containing Superoxide Dismutase," Jpn. Kokai Tokkyo Koho, 8107,720, 27 Jan. 1981,(cited in Chem. Abstracts, vol. 94:145386f, 1981).
Kwa, "Glycyl-L-Histidyl-L-Lysine: Synthesis of Analogs and NMR Studies," Ph. D. Thesis, University of Washington, 1983.
Loker, "Synthesis of Blood Serum Peptide Cell Growth Factors," Ph.D. Thesis, University of Washington, 1980.
Pickart, "The Biological Effects and Mechanism of Action of the Plasma Tripeptide Glycyl-L-Histidyl-L-Lysine," *Lymphonkines*, 8, pp. 425–446, 1983.
Poole et al., "Stimulation of Rat Peritoneal Mast Cell Migration by Tumor-Derived Peptides," *Cancer Research*, 43, pp. 5857–5861, 1983.
Raju et al., "Ceruloplasmin, Copper Ions, and Angiogenesis," *JUNCI*, 69(5), pp. 1183–1188, 1982.
Freedman et al., "Structure of the Glycl-L-Histidyl-l-Lysiine-Copper(II) Complex in Solution," *Biochemistry*, 21, pp. 4540–4544, 1982.
Kwa et al., "PMR Studies of CU(II) and Zn(II) Interaction with Glycyl-L-Histidyl-L-Lysine and Related Peptides," *Peptides: Structure and Function*, 8, pp. 805–808, 1983.
Perkins et al., "The Structure of a Copper Complex of the Growth Factor Glycyl-L-Histidyl-L-Lysine at 1.1 A Resolution," *Inorganica Chimica Acta*, 82, pp. 93–99, 1984.
Kimoto et al., "Enhancement of Antitumor Activity of Ascorbate Against Ehrlich Ascites Tumor Cells by the Copper: Glycylglycylhistidine Complex," *Cancer Research*, 43, pp. 824–828, 1963.
Sorenson, "Copper Complexes: A Physiological Approach to Treatment of Chronic Diseases," *Comprehensive Therapy*, 11(4), pp. 49–64, 1985.
Pickart et al., "Inhibition of the Growth of Cultured Cells and an Implanted Fibrosarcoma by Aroylhydrazone Analogs of the Gly-His-Lys-Cu(II) Complex," *Biochem. Pharmacol.*, 32(24), pp. 3868–3871, 1983.
Pickert et al., "Growth-Modulating Plasma Tripeptide May Function By Facilitating Copper Uptake Into Cells," *Nature*, 288, pp. 715–717, 1980.
Natural Healing Annual, 1986, p. 38, (Edit M. Bricklin, Prevention Magazine, Rodale Press, Emmaus, PA).
Pickart et al., "A Synthetic Tripeptide which Increases Survival of Normal Liver Cells, and Stimulates Growth in Hepatoma Cells," *Biochem. Biophys. Res. Commun.*, 54(2), p. 526-6, 1973.

*Primary Examiner*—Delbert R. Phillips
*Attorney, Agent, or Firm*—Seed and Berry

[57] ABSTRACT

Derivatives of GHL-Cu possessing greater resistance to proteolytic enzyme breakdown are disclosed. These derivatives can be taliored to increase their fat solubility, making them more useful in the formation of pharmaceutical creams and gels. Further, the derivatives of the present invention possess significant superoxide dismustase activity, making them useful for enhancing the wound-healing process in animals.

9 Claims, No Drawings

CHEMICAL DERIVATIVES OF GHL-CU

CROSS-REFERENCE TO RELATED APPLICATION

This application is a continuation of U.S. Ser. No. 040,460, filed Apr. 20, 1987 now abandoned, which application is a continuation-in-part of U.S. Ser. No. 699,824, filed Feb. 8, 1985, which application issued as U.S. Pat. No. 4,665,054.

TECHNICAL FIELD

The present invention relates to chemical derivatives of glycyl-L-histidyl-L-lysine: copper (II) (GHL-Cu) in general, and more specifically, to GHL-Cu derivatives exhibiting particularly useful biological activities.

BACKGROUND ART

GHL-Cu is a human blood factor present in trace amounts and thought to be involved in transport and cellular uptake of copper (Pickart, L., Lymphokines 8: 425–446, 1983). Recently, applicants have discovered that GHL-Cu may be used to enhance the wound-healing process and reduce inflammation in injured animals. This discovery is the subject of applicant's U.S. patent application filed Jan. 24, 1985.

The healing of many types of traumatic tissue damage and of aging associated with degenerative conditions is delayed by the excessive production of superoxide anion. After wounding or traumatic tissue injury, cells of the immune system invade the damaged area and secrete copious quantities of toxic oxygen radicals to kill invading bacteria. Often, in cases of impaired healing, the production of superoxide anion further damages tissues and brings in a new influx of immunological cells, thereby creating a vicious circle of damaging events which can greatly delay the sequence within the normal healing process. To obtain proper healing of damaged tissue, it is generally necessary to terminate the production of superoxide anion in the afflicted area.

GHL-Cu possesses significant superoxide dismutase activity, allowing it to detoxify the tissue-damaging superoxide anion. Further, GHL-Cu also inhibits platelet aggregation and the production of the vasoconstrictive and the thrombosis-inducing hormone, thromboxane. GHL-Cu accelerates the healing of wounds in rats, mice and pigs and possesses anti-inflammatory actions in standard rat inflammation models.

However, although valuable, GHL-Cu is susceptible to breakdown by proteolytic enzymes called carboxypeptidases and is poorly soluble in fatty tissues.

Accordingly, it is a primary object of the present invention to improve the resistance of GHL-Cu to breakdown and further to increase the fatty tissue solubility of GHL-Cu, resulting in a more useful form of the molecule.

DISCLOSURE OF THE INVENTION

Briefly stated, the present invention discloses various derivatives of GHL-Cu which possess greater resistance to proteolytic enzyme breakdown and which can be tailored to increase the fat solubility thereof. The derivatives have the general formula glycyl-L-histidyl-L-lysine-R: copper (II), where R=NH$_2$ or a functional group having from 1 to 18 carbon atoms. "R" may be a benzyl radical or an aromatic carbon radical having from 6 to 12 carbon atoms.

Alternatively, R may be an aliphatic carbon radical having from 1 to 18 carbon atoms. The aliphatic carbon radical may be a methyl radical or the aliphatic carbon radical may further be an unbranched chain. The unbranched chain may be an n-octyl radical, an n-palmityl radical, or an n-stearyl radical.

In addition, the present invention discloses a method for enhancing the wound-healing process in an animal comprising administering to the animal a therapeutically effective amount of a composition containing a derivative of GHL-Cu. The derivatives have the general formula glycyl-L-histidyl-L-lysine-R: copper (II), where R=NH$_2$ or a functional group having from 1 to 18 carbon atoms. "R" may be a benzyl radical or an aromatic carbon radical having from 6 to 12 carbon atoms. Alternatively, R may be an aliphatic carbon radical having from 1 to 18 carbon atoms.

A further aspect of the invention discloses a method inhibiting the production of thromboxane by platelets in animals comprising administering to the animal an therapeutically effective amount of a composition containing a derivative of GHL-Cu. The derivatives have the general formula glycyl-L-histidyl-L-lysine-R: copper (II), where R=NH$_2$ or a functional group having from 1 to 18 carbon atoms.

Other aspects of the present invention will become evident upon reference to the following detailed description.

BEST MODE FOR CARRYING OUT THE INVENTION

As noted above, GHL-Cu possesses significant superoxide dismutase activity, allowing it to detoxify tissue-damaging sueroxide anion. However, GHL-Cu is susceptible to breakdown by proteolytic enzymes and is poorly soluble in fatty tissues. However, as described herein, various derivatives of GHL-Cu retain their superoxide dismutase activity while exhibiting greater resistance to proteolytic breakdown. Further, these derivatives increase the fatty tissue solubility of GHL-Cu, resulting in a form of the molecule which is more useful in the formation of pharmaceutical creams and gels.

The derivatives of the present invention may be prepared by esterification, by the removal of a water molecule, or the addition of a group (either an alcohol such as octanol, methanol, or benzyl alcohol or NH$_3$) to the carboxylic acid terminus of GHL, resulting in the formation of the more lipophilic derivative. This increases the fat solubility by (1) removal of the electric charge associated with the carboxylic acid group and (2) the introduction of hydrophilic groups into the molecule.

The overall chemical reaction in this transformation may be characterized as:

$$\text{GHL-OH} + \text{R-H} \rightarrow \text{GHL-R} + \text{H}_2\text{O}$$

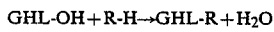

In practice, the reaction is most readily carried out by adding the R group to the amino acid lysine prior to the combination of lysine with the other two amino acids of GHL. After the formation and isolation of GHL-R, the copper (II) is chelated to the molecule to form the bioactive complex.

The overall reaction to form the more lipophilic derivatives of GHL-Cu may be charcterized:
(1) lysine-OH + R-H → lysine-R + H$_2$O
(2) lysine-R + blocked L-histidine → blocked L-histidine-L-lysine-R (3) blocked L-histidine-L-lysine-R + blocked-glycine→ blocked glycyl-L-histidine-L-lysine-R (4) blocked glycyl-L-histidine-L-lysine-R→glycyl-L-histidine-L-lysine-R (5) glycyl-L-histidine-L-lysine-R + copper (II)→glycyl-L-histidine-L-lysine-R: copper (II)

The derivatives of the present invention are useful for enhancing the wound-healing process in animals. Briefly stated, wound healing is a highly specific biological response involving many closely coordinated events which must be kept in balance for proper healing. Immunological cells must clear bacteria and damaged tissue from the wound, and then allow other processes to occur, such as the re-epithiliazation of the lost skin, deposition of fibroblastic cells of the structural protein collagen to provide temporary wound strength, the regrowth of blood vessel, lymphatic and nervous networks, the contraction of the wound area, and the reestablishment of hair follicles in the newly formed skin. If any process improperly predominates, healing is partial and inadequate. For example, excessive collagen deposition results in permanent scarring while excessive blood vessel growth may give rise to hemangioma.

Due to the complex interaction of various processes in the healing of wounds, a superior method for enhancing the wound-healing process should include the proper maintenance of each of these processes without evoking an antigenic response. The present invention exemplifies such a method, and further provides other related advantages.

The present invention utilizes a therapeutically effective amount of a composition consisting essentially of derivatives of GHL-Cu to enhance the wound-healing process in animals. The derivatives of GHL-Cu described herein possess significant superoxide dismutase activity at physiological pH, and like other superoxide dismutases, have anti-inflammatory and wound-healing properties. The derivatives of GHL-Cu also inhibit the production of the vasoconstrictive and thrombosis-inducing hormone, thromboxane.

Moreover, the derivatives of GHL-Cu described herein have advantages over GHL-Cu. In particular, the derivatives are more lipophilic than GHL-Cu, resulting in greater solubility in creams and gels useful in the treatment of wounds. Furthermore, the derivatives of the present invention display a greater resistance to proteolytic breakdown by the enzyme carboxypeptidase, allowing sustained activity of the derivatives for more effective wound healing.

To summarize the examples which follow, Example I illustrates the synthesis of glycyl-L-histidyl-L-lysine benzyl ester: copper (II). Example II describes the preparation of glycyl-L-histidyl-L-lysine amide: copper (II). Example III demonstrates the synthesis of glycyl-L-histidyl-L-lysine n-octyl ester: copper (II). Example IV describes the preparation of glycyl-L-histidyl-L-lysine methyl ester: copper (II). Example V illustrates (A) the synthesis of glycyl-L-histidyl-L-lysine n-stearyl ester: copper (II), and (B) its synthesis by an alternative procedure. Based upon either procedure, one skilled in the art could substitute n-palmityl alcohol (16 carbons) for the n-stearyl alcohol (18 carbons) to yield glycyl-L-histidyl-L-lysine n-palmityl ester: copper (II). Example VI demonstrates the superoxide dismutase activity of GHL-Cu derivatives. Example VII illustrates (A) the wound-healing activity and (B) the anti-thromboxane activity of GHL-Cu derivatives. Example VIII demonstrates the resistance to proteolytic enzyme breakdown of GHL-Cu derivatives.

The following examples are offered by way of illustration and not by way of limitation.

EXAMPLES

Sources of chemicals. Chemicals and peptide intermediates utilized in the following examples may be purchased from the following suppliers: Sigma Chemical Co. (St. Louis, MO); Peninsula Laboratories (San Carlos, CA); Aldridge Chemical Co. (Milwaukee, WI); Vega Biochemicals (Tucson, AZ); Pierce Chemical Co. (Rockford, IL); Research Biochemicals (Cleveland, OH); Van Waters and Rogers (South San Francisco, CA); Bachem, Inc. (Torrance, CA).

EXAMPLE I

Synthesis of glycyl-L-histidyl-L-lysine benzyl ester: copper (II)

$N^e$-benzyloxycaronyl-L-lysine benzyl ester was dissolved in 1:1 hexane-ethyl acetate and coupled to $N^a$-t-butyloxycarbonyl-$N^{im}$-benzyloxycarbonyl-L-histidine using dicyclohexylcarbodiimide as a coupling agent. Sodium bicarbonate (10%) was added and the product extracted into the organic layer. The product, $N^a$-t-butyloxycarbonyl-$N^{im}$-benzyloxycarbonyl-L-histidyl-$N^e$-benzyloxycarbonyl-L-lysine benzyl ester, was crystallized from solution. The N-terminal group of the blocked dipeptide was removed by stirring in 50% trifluoroacetic acid in dichloromethane for 30 minutes, then vacuum evaporated. The product, $N^{im}$-benzyloxycarbonyl-L-histidyl-$N^e$-benzoylcarbonyl-L-lysine benzyl ester, was coupled to t-butyloxycarbonylglycine with dicyclohexylcarbodiimide as a coupling agent. Blocking groups were removed by catalytic hydrogenation using 10% palladium on carbon in glacial acetic acid. After lyophilization, the product, glycyl-L-histidyl-L-lysine benzyl ester, was dissolved in water and purified by ion-exchange chromatography on Dowex 50 X-4 cation-exchange resin and elution with 0.1M ammonium hydroxide, the eluate being immediately neutralized with acetic acid. A further passage through an anion-exchange column BioRex 63 at neutral pH removed breakdown products with free carboxylic acid groups.

The glycyl-L-histidyl-L-lysine benzyl ester was dissolved in water with equimolar copper acetate added. The pH was raised to neutrality with sodium hydroxide. The solution was centrifuged at 20,000 xg for 1 at 3° C. to remove poorly water-soluble material. The supernatant was lyophilized to obtain glycyl-L-histidyl-L-lysine benzyl ester: copper (II).

EXAMPLE II

Synthesis of glycyl-L-histidyl-L-lysine amide: copper (II)

$N^a$-t-butyloxycarbonyl-$N^e$-benzyloxycarbonyl-L-lysine was dissolved in ethyl acetate and esterified with p-nitrophenol using dicyclohexylcarbodiimide as a coupling agent. Sodium bicarbonate (10%) was added and the product extracted into the organic layer and crystallized from solution, then added to aqueous ammonium hydroxide to form $N^a$-t-butyloxycarbonyl-$N_e$-benzyloxycarbonyl-L-lysine amide.

The amide was dissolved in 50% trifluoroacetic acid in dichloromethane for 30 minutes to form $N^e$-benzyloxycarbonyl-L-lysine amide, which was isolated after flash evaporation of the solvents. $N^e$-benzyloxycarbonyl-L-lysine amide was dissolved in N,N-dimethylformamide and N-methylmorpholine, then added dropwise to $N^a$-t-butyloxycarbonyl-$N^{im}$-benzyloxycarbonyl-L-histidine in N-methylmorpholine and isobutyl chloroformate in tetrahydrofuran. After stirring for one hour and addition of 5% sodium bicarbonate, the product, $N^a$-t-butyloxycarbonyl-$N^{im}$-benzyloxycarbonyl-L-histidyl-$N^e$-benzyloxycarbonyl-L-lysine amide, was extracted into ethyl acetate. The amino terminus of the blocked dipeptide was deblocked with 50% trifluoroacetic acid in dichloromethane for 30 minutes and flash evaporated to obtain the product, which was then coupled to benzyloxycarbonylglycine using dicyclohexylcarbodiimide to give the blocked tripeptide. Blocking groups were removed by catalytic hydrogenation using 10% palladium on carbon in glacial acetic acid. After lyophilization, the product, glycyl-L-histidyl-L-lysine amide, was dissolved in water and purified by ion-exchange chromatography on Dowex 50 X-4 cation-exchange resin and elution with 0.1M ammonium hydroxide, the eluate being immediately neutralized with acetic acid. A further passage through an anion-exchange column BioRex 63 at neutral pH removed breakdown product.

The final product, glycyl-L-histidyl-L-lysine amide, was dissolved in water and an equimolar amount of copper acetate added. The pH was raised to neutrality with sodium hydroxide. The solution was centrifuged at 20,000 g for 1 hour at 3° C. to remove poorly water-soluble material. The supernatant was lyophilized to obtain glycyl-L-histidyl-L-lysine amide: copper (II).

EXAMPLE III

Synthesis of glycyl-L-histidyl-L-lysine n-octyl ester: copper (II)

A mixture of $N^e$-benzyloxycarbonyl-L-lysine, n-octanol, benzene, and p-toluenesulfonic acid monohydrate was refluxed overnight using a Dean-Stark trap to remove water. After cooling, dry ethyl ether was added. The solution was then allowed to precipitate at 0° C. overnight. A portion of the precipitated solid was added to 50 ml potassium carbonate solution and 50 ml dichloromethane. After extraction, the layers were separated and the organic phase washed with water and brine, then dried with anhydrous magnesium sulfate. Filtration, evaporation and purification by flash column chromatography gave n-octyl $N^e$-benzyloxycarbonyl-L-lysinate. The product was dissolved in tetrahydrofuran and mixed with $N^a$-t-butyloxycarbonyl-L-$N^{im}$-benzyloxycarbonyl-L-histidine, isobutyl chloroformate and N-methylmorpholine. After evaporation, water and ethyl acetate were added. The product was extracted into the organic phase, which was dried with anhydrous magnesium sulfate. Filtration, evaporation and purification by flash column chromatography gave n-octyl $N^a$-t-butyloxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-octyl $N^{im}$-benzyloxycarbonyl-L-histidyl-$N^e$-benzyloxycarbonyl-L-lysinate. This was dissolved in tetrahydrofuran, and isobutyl chloroformate, N-methylmorpholine and benzyloxycarbonylglycine were added to form n-octyl benzyloxycarbonylglycyl-$N^{im}$-benzyloxycarbonyl-L-histidyl-$N^e$-benzyloxycarbonyl-L-lysinate. This was dissolved in glacial acetic acid and hydrogenated overnight.

The resultant n-octyl ester of glycyl-L-histidyl-L-lysine was converted to the copper complex by the addition of an equimolar quantity of copper diacetate. The pH was raised to neutrality with sodium hydroxide. The solution was centrifuged at 20,000 g for 1 hour at 3° C. to remove poorly water-soluble material. The supernatant was lyophilized to obtain glycyl-L-histidyl-L-lysine n-octyl ester: copper (II).

EXAMPLE IV

Synthesis of glycyl-L-histidyl-L-lysine methyl ester: copper (II)

$N^e$-benzyloxycarbonyl-L-lysine methyl ester hydrochloride was neutralized with one equivalent of N-methylmorpholine. It was then coupled with $N_a$-t-butyloxycarbonyl-$N^{im}$-benzyloxymethyl-L-histidine using a mixture of dicyclohexylcarbodiimide and 1-hydroxybenzotriazole as a coupling agent in tetrahydrofuran. The reaction was allowed to proceed overnight, filtered, and the solvent evaporated. Ethyl acetate was added, and the mixture was refiltered. Aqueous work-up of the filtrate followed by evaporation and purification by flash column chromatography, using ethyl acetate/methanol as eluant, resulted in methyl $N_a$-t-butyloxycarbonyl-$N^{im}$-benzyloxymethyl-L-histidyl-$N^e$-benzyloxycarbonyl-L-lysinate. The N-terminal blocking group of the dipeptide was removed by stirring in 50% trifluoroacetic acid in dichloromethane for 30 minutes, then vacuum evaporated. The product, methyl $N^{im}$-benzyloxymethyl-L-histidyl-$N^e$-benzyloxycarbonyl-L-lysinate, was neutralized with dry N-methylmorpholine and coupled to benzyloxycarbonylglycine using isobutyl chloroformate. The reaction was allowed to proceed for two hours, evaporated and redissolved in ethyl acetate. After aqueous work-up, filtration, and evaporation, the product was purified by column chromatography. The blocking groups were removed from the benzyloxycarbonylglycyl-$N^{im}$-benzyloxymethyl-L-histidyl-$N_e$-benzyloxycarbonyl-L-lysine methyl ester by catalytic hydrogenation using Pd-C in methanol/acetic acid. After lyophilization, the product, glycyl-L-histidyl-L-lysine methyl ester, was dissolved in propanol/acetic acid/water and purified by column chromatography on a cellulose column. The final product, glycyl-L-histidyl-L-lysine methyl ester, was dissolved in water with an equimolar amount of copper acetate added. The pH was raised to neutrality with sodium hydroxide. The solution was then centrifuged at 20,000 g for 1 hour at 3° C. to remove poorly water-soluble material. The supernatant was lyophilized to obtain glycyl-L-histidyl-L-lysine methyl ester: copper (II).

EXAMPLE V

A. Synthesis of glycyl-L-histidyl-L-lysine n-stearyl ester: copper (II)

A mixture of $N^e$-benzyloxycarbonyl-L-lysine, n-stearyl alcohol, benzene, and p-toluenesulfonic acid monohydrate was refluxed overnight using a Dean-Stark trap to remove water. After cooling, dry propyl ether was added to increase the total volume six-fold. The product was allowed to precipitate at 0° C. overnight and filtered. A portion of the filtrate was added to 50 ml potassium carbonate and 50 ml dichloromethane. After extraction, the layers were separated, and the organic phase was washed with water and brine, then dried with anhydrous magnesium sulfate. Filtration, evaporation and purification by flash column chromatography gave n-stearyl N$^e$-benzyloxycarbonyl-L-lysinate. The product was dissolved in tetrahydrofuran and mixed with N$^a$-t-butyloxycarbonyl-N$^{im}$-benzyloxycarbonyl-L-histidine and isobutyl chloroformate and N-methylmorpholine. After evaporation, water and propyl acetate were added and the product was extracted into the organic phase, then dried with anhydrous magnesium sulfate. Filtration, evaporation and purification by flash column chromatography gave n-stearyl N$^a$-t-butyloxycarbonyl-N$^{im}$-benzyloxycarbonyl-L-histidyl-N$^e$-benzyloxycarbonyl-L-lysinate.

The product was dissolved in 50% trifluoroacetic acid in dichloromethane for 30 minutes, then evaporated, forming n-stearyl N$^{im}$-benzyloxycarbonyl-L-histidyl-N$^e$-benzyloxycarbonyl-L-lysinate, which was dissolved in tetrahydrofuran, isobutyl chloroformate, N-methylmorpholine and benzyloxycarbonylglycine to form n-stearyl benzyloxycarbonylglycyl-N$^{im}$-benzyloxycarbonyl-L-histidyl-N$^e$-benzyloxycarbonyl-L-lysinate. The product was dissolved in 50% trifluoroacetic acid in dichloromethane for 30 minutes, then evaporated, forming n-stearyl ester glycyl-L-histidyl-L-lysine.

Th resultant molecule, glycyl-L-histidyl-L-lysine n-stearyl ester, was converted to the copper complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

B. Alternative synthesis of glycyl-L-histidyl-L-lysine n-stearyl ster: copper (II)

N( )-benzyloxycarbonyl-L-lysine, n-stearyl alcohol, p-toluenesulfonic acid monohydrate, and benzene are refluxed together using a Dean-Stark trap to azeotropically remove the evolved water. Afer cooling to room temperature and then adding dry ethyl ether, n-stearyl N( )-benzyloxycarbonyl-L-lysinate p-toluenesulfonate salt is collected by filtration, treated with 2M aqueous potassium bicarbonate solution, and extracted into dichloromethane. Evaporation gives the free amine, which is redissolved in dry tetrahydrofuran (THF) and added to a stirring solution of N( )-t-butyloxycarbonyl-N(im)-benzyloxycarbonyl-L-histidine, N-methylmorpholine, and isobutyl chloroformate in dry THF at −15° C. The resulting fully protected dipeptide ester is treated with 1/1 trifluoroacetic acid/dichloromethane at room temperature, neutralized with saturated aqueous sodium bicarbonate solution, and extracted into ethyl acetate. Evaporation gives the partially deblocked dipeptide, which is redissolved in dry THF and added to a stirring solution of benzyloxycarbonylglycine, N-methylmorpholine and isobutyl chloroformate in dry THF at −15° C. The formed, fully protected tripeptide ester is totally deblocked by treatment with hydrogen gas in glacial acetic acid at room temperature in the presence of Pd-C catalyst. Filtration, evaporation and purification on a microcrystalline cellulose column followed by lyophilization give the desired tripeptide ester as its triacetate salt.

The resultant molecule, glycyl-L-histidyl-L-lysine n-stearyl ester, was converted to the copper complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

EXAMPLE VI

Superoxide dismutase activities in GHL-Cu derivatives

All of the more lipophilic derivatives of GHL-Cu, some of which are shown below, possessed superoxide dismutase activities similar to biological GHL-Cu when assayed using the auto-oxidation of 6-hydroxydopamine method of Heikkla and Cabbat (Anal. Biochem. 75: 356–362, 1972).

| Compound Tested | Percent of GHL-Cu Activity on a Molar Basis |
|---|---|
| GHL-Cu (control) | 100 |
| glycyl-L-histidyl-L-lysine benzyl ester: copper (II) | 96 |
| glycyl-L-histidyl-L-lysine n-octyl ester: copper (II) | 99 |
| glycyl-L-histidyl-L-lysine amide: copper (II) | 109 |
| glycyl-L-histidyl-L-lysine methyl ester: copper (II) | 97 |

EXAMPLE VII

Examples of useful actions of GHL-Cu derivatives (A) Wound-healing

In mice, incision wounds on the flanks (six 1.5 cm wounds per animal) were swabbed daily with either a solution containing GHL-Cu (100 micrograms per mL) in phosphate-buffered saline (PBS) or PBS alone (6 animals each group). After 5 days, the wounds were scored 1.0 for complete closure, 0.5 for partial closure, and 0.0 for nonclosure.

Effect of GHL-Cu and selected derivatives on healing of wounds in mice

| | Score per wound |
|---|---|
| Control | 0.21 ± 0.06 |
| GHL-Cu | 0.60 ± 0.11 |
| glycyl-L-histidyl-L-lysine benzyl ester: copper (II) | 0.61 ± 0.15 |
| glycyl-L-histidyl-L-lysine n-octyl ester: copper (II) | 0.54 ± 0.12 |
| glycyl-L-histidyl-L-lysine amide: copper (II) | 0.39 ± 0.07 |

The results demonstrate that application of the GHL-Cu derivatives of the present invention (including glycl-L-histidyl-L-lysine M-stearyl ester: copper (II), and Glycyl-L-histidyl-L-lysine n-palmityl ester: copper (II)) to a wound significantly enhances the wound-healing process.

(B) Anti-thromboxane activities of GHL-Cu and derivatives

Dog platelets in plasma were aggregated with ADP and collagen. Production of thromboxane $B_2$ was measured by radioimmunoassay (New England Nuclear Thromboxane Assay Kit, Boston, MA).

| Compound Tested | Inhibition of Platelet Thromboxane Production Induced by 1 Microgram Per Milliliter |
|---|---|
| GHL-Cu | 85 ± 6 |
| glycyl-L-histidyl-L-lysine benzyl ester: copper (II) | 89 ± 6 |
| glycyl-L-histidyl-L-lysine n-octyl ester: copper (II) | 82 ± 4 |
| glycyl-L-histidyl-L-lysine amide: copper (II) | 42 ± 4 |

These results demonstrate that the GHL-Cu derivatives of the present invention, some of which are described above, significantly inhibit the production of thromboxane by platelets, thereby allowing an optimal flow of blood to the wound area.

EXAMPLE VIII

Resistance to breakdown by carboxypeptidase of GHL-Cu and derivatives

All of the more lipophilic peptide analogs of GHL, some of which are set forth below, possessed more resistance to proteolytic breakdown by the enzyme carboxypeptidase when assayed using the method of Schlesinger et al., *Experientia* 33: 324-324 (1977).

| Compound Tested | Percent of Breakdown After 1 Minute |
|---|---|
| glycyl-L-histidyl-L-lysine (control) | 97 |
| glycyl-L-histidyl-L-lysine benzyl ester | 6 |
| glycyl-L-histidyl-L-lysine n-octyl ester | 19 |
| glycyl-L-histidyl-L-lysine amide | 32 |
| glycyl-L-histidyl-L-lysine methyl ester | 41 |

Example VIII demonstrates the resistance of GHL and GHL derivatives to proteolytic breakdown, in vitro.

In the body, GHL is in equilibrium with GHL-Cu due to dynamic copper binding and exchange reactions. In its metal-free form, GHL becomes sensitive to proteolytic breakdown and inactivation by the enzyme carboxypeptidase. As GHL is degraded, the amount of GHL-Cu is decreased.

The derivatives of GHL also bind to copper, and in the body, the metal-free forms would exist in equilibrium with the copper complexed forms. Degradation of the metal-free forms would decrease the amount of complexed forms available. Example VIII demonstrates that the metal-free derivatives of GHL are less susceptible to proteolytic breakdown than metal-free GHL. One explanation for this phenomenon is that the "R" group attached to the carboxyterminus of GHL alters the molecular confirmation, thus preventing proper enzymatic recognition of the GHL derivatives by proteolytic enzymes.

Accordingly, the in vivo degradation of the derivatives of GHL-Cu should be markedly reduced. This attribute would allow the derivatives of GHL-Cu to be more effective than GHL-Cu in a bioactive environment containing degradation mechanisms.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

I claim:

1. Derivatives of GHL-Cu which possess wound-healing activity and having the general formula:

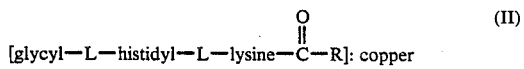

wherein R is selected from alkoxy moieties containing from 16 to 18 carbon atoms.

2. The derivative of claim 1 wherein the carbon portion of the alkoxy moiety is an n-stearyl moiety.

3. The derivative of claim 1 wherein the carbon portion of the alkoxy moiety is an n-palmityl moiety.

4. A method for enhancing the wound-healing process in an animal, comprising administering to the animal a therapeutically effective amount of a composition containing a derivative of GHL-Cu, said derivatives of GHL-Cu having the general formula:

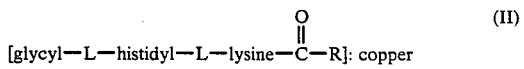

wherein R is selected from alkoxy moieties containing from 16 to 18 carbon atoms.

5. The derivative of claim 4 wherein the carbon portion of the alkoxy moiety is an n-stearyl moiety.

6. The derivative of claim 4 wherein the carbon portion of the alkoxy moiety is an n-palmityl moiety.

7. A method of inhibiting the production of thromboxane by platelets in animals, comprising administering to the animal a therapeutically effective amount of a composition containing a derivative of GHL-Cu, said derivatives of GHL-Cu having the general formula:

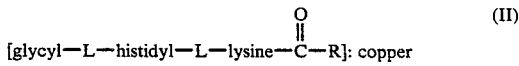

wherein R is selected from alkoxy moieties containing from 16 to 18 carbon atoms.

8. The derivative of claim 7 wherein the carbon portion of the alkoxy moiety is an n-stearyl moiety.

9. The derivative of claim 7 wherein the carbon portion of the alkoxy moiety is an n-palmityl moiety.

UNITED STATES PATENT AND TRADEMARK OFFICE
CERTIFICATE OF CORRECTION

PATENT NO. : 4,877,770

DATED : October 31, 1989

INVENTOR(S) : Manfred Lutz and Bernd Reimer

It is certified that error appears in the above-identified patent and that said Letters Patent is hereby corrected as shown below:

The term of this patent subsequent to April 12, 2000, has been disclaimed.

Signed and Sealed this

Fifth Day of December, 1989

Attest:

JEFFREY M. SAMUELS

Attesting Officer

Acting Commissioner of Patents and Trademarks